(12) United States Patent
Kerr et al.

(10) Patent No.: US 9,308,297 B2
(45) Date of Patent: Apr. 12, 2016

(54) POROUS BIOCOMPATIBLE POLYMER MATERIAL AND METHODS

(71) Applicant: DePuy Synthes Products, Inc., Raynham, MA (US)

(72) Inventors: Sean Hamilton Kerr, Oreland, PA (US); Ali Recber, Piscataway, NJ (US); Thomas Pepe, Turnersville, NJ (US); Dominique Messerli, Downingtown, PA (US); Lawton Laurence, West Chester, PA (US); Ryan Walsh, Douglassville, PA (US); Thomas Kueenzi, Downingtown, PA (US); Brandon Randall, Chester Springs, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 105 days.

(21) Appl. No.: 13/967,422

(22) Filed: Aug. 15, 2013

(65) Prior Publication Data

US 2014/0207237 A1    Jul. 24, 2014

Related U.S. Application Data

(63) Continuation of application No. 12/666,216, filed as application No. PCT/US2009/000604 on Jan. 30, 2009, now Pat. No. 8,530,560.

(60) Provisional application No. 61/025,426, filed on Feb. 1, 2008.

(51) Int. Cl.

| | |
|---|---|
| *C04B 28/14* | (2006.01) |
| *A61L 27/56* | (2006.01) |
| *A61F 2/44* | (2006.01) |
| *A61N 1/362* | (2006.01) |
| *C08J 9/24* | (2006.01) |
| *C08J 9/26* | (2006.01) |
| *A61L 27/18* | (2006.01) |
| *C08G 65/00* | (2006.01) |
| *A61B 17/86* | (2006.01) |
| *A61F 2/28* | (2006.01) |
| *A61F 2/30* | (2006.01) |

(52) U.S. Cl.
CPC .............. *A61L 27/56* (2013.01); *A61F 2/4455* (2013.01); *A61L 27/18* (2013.01); *A61N 1/3622* (2013.01); *C08G 65/00* (2013.01); *C08J 9/24* (2013.01); *C08J 9/26* (2013.01); *A61B 17/86* (2013.01); *A61F 2002/2817* (2013.01); *A61F 2002/3008* (2013.01); *A61F 2002/30062* (2013.01); *A61F 2002/30064* (2013.01); *A61F 2002/3092* (2013.01); *A61F 2002/3097* (2013.01); *A61F 2002/30387* (2013.01); *A61F 2002/30426* (2013.01); *A61F 2002/30578* (2013.01); *A61F 2002/30604* (2013.01); *A61F 2002/30841* (2013.01); *A61F 2210/0004* (2013.01); *A61F 2220/0025* (2013.01); *A61F 2250/0098* (2013.01); *A61F 2310/00796* (2013.01); *A61F 2310/00976* (2013.01)

(58) Field of Classification Search
CPC ........................................................ C08J 9/26
USPC ........................................................ 524/423
See application file for complete search history.

(56) References Cited

U.S. PATENT DOCUMENTS

| | | | |
|---|---|---|---|
| 4,430,760 A | 2/1984 | Smestad | |
| 8,530,560 B2 * | 9/2013 | Kerr ........................ | C08G 65/00 424/490 |
| 2002/0007209 A1 * | 1/2002 | Scheerder ............... | A61F 2/915 623/1.15 |
| 2002/0099449 A1 * | 7/2002 | Speitling .................... | 623/23.72 |
| 2002/0143403 A1 * | 10/2002 | Vaidyanathan et al. ... | 623/23.51 |
| 2003/0031698 A1 | 2/2003 | Roeder et al. | |
| 2004/0043135 A1 * | 3/2004 | Han ........................ | A61L 27/18 427/2.1 |
| 2005/0042288 A1 | 2/2005 | Koblish et al. | |
| 2005/0112397 A1 | 5/2005 | Rolfe et al. | |
| 2006/0052479 A1 | 3/2006 | Cougoulic | |
| 2006/0136071 A1 * | 6/2006 | Maspero ............. | A61L 27/3847 623/23.76 |
| 2006/0224242 A1 * | 10/2006 | Swords ............... | A61B 17/8085 623/17.19 |
| 2007/0093912 A1 * | 4/2007 | Borden ..................... | A61F 2/28 623/23.75 |
| 2008/0206297 A1 * | 8/2008 | Roeder ..................... | A61F 2/28 424/422 |
| 2008/0234400 A1 | 9/2008 | Allmendinger et al. | |

FOREIGN PATENT DOCUMENTS

| | | |
|---|---|---|
| CN | 1732025 | 2/2006 |
| DE | 10 2005 039976 | 3/2007 |
| EP | 0 889 928 | 3/2000 |
| EP | 1 647 242 | 5/2008 |
| JP | A-58-023835 | 2/1983 |
| JP | A-59-197439 | 11/1984 |
| JP | 02-224660 | 9/1990 |
| JP | 04-146762 | 5/1992 |
| JP | 2001-204751 | 7/2001 |

(Continued)

OTHER PUBLICATIONS

Chinese Patent Application No. 200980103902.5, Office Action, dated Apr. 25, 2012, 8 pages.

(Continued)

*Primary Examiner* — Doris Lee
(74) *Attorney, Agent, or Firm* — Baker & Hostetler LLP

(57) ABSTRACT

Embodiments described include devices and methods for forming a porous polymer material. Devices disclosed and formed using the methods described a spacer for spinal fusion, craniomaxillofacial (CMF) structures, and other structures for tissue implants.

21 Claims, 21 Drawing Sheets

(56) References Cited

FOREIGN PATENT DOCUMENTS

| | | | |
|---|---|---|---|
| JP | 2000-508013 | | 6/2002 |
| JP | 2003-210570 | | 7/2003 |
| JP | A-2006-158953 | | 6/2006 |
| WO | WO 2007/051120 | | 5/2007 |
| WO | WO 2007 051307 | * | 5/2007 |
| WO | WO 2009/099559 | | 8/2009 |

OTHER PUBLICATIONS

Chinese Patent Application No. 200980103902.5: office action dated Apr. 25, 2012.
International Application No. PCT/US2009/000604: International Search Report dated Jan. 28, 2010, 4 pages.
Japanese Patent Application No. 2010-545025: office action dated Oct. 8, 2013, 4 pages.

* cited by examiner

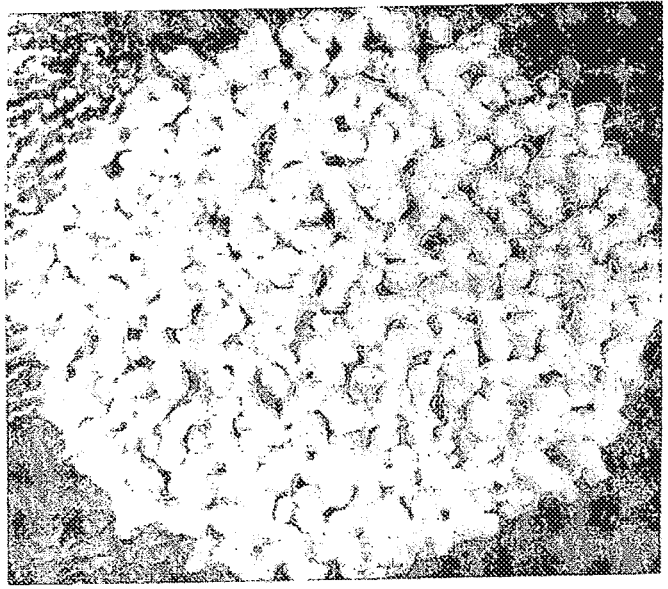
PEEK granules (0.5-1mm) with β-TCP after 5 mins @ 400 degrees C
FIG. 1A
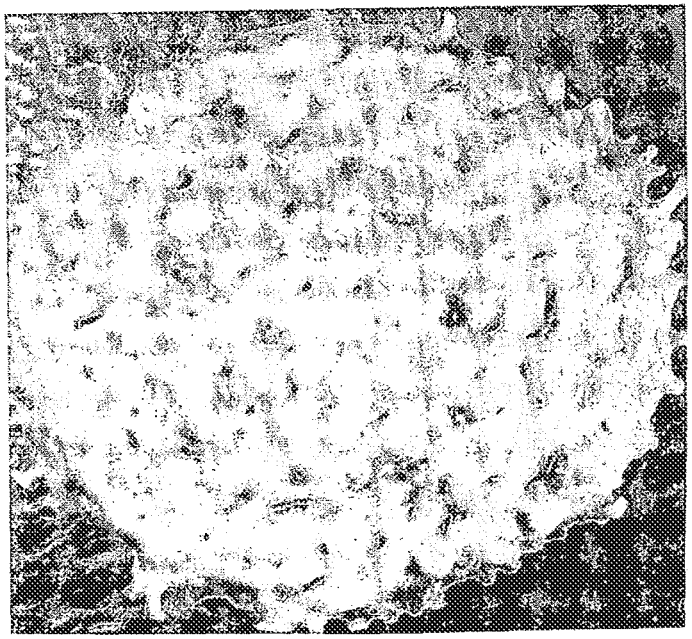
PEEK granules (0.5-1mm) after 5 mins @ 400 degrees C
FIG. 1B – Prior Art

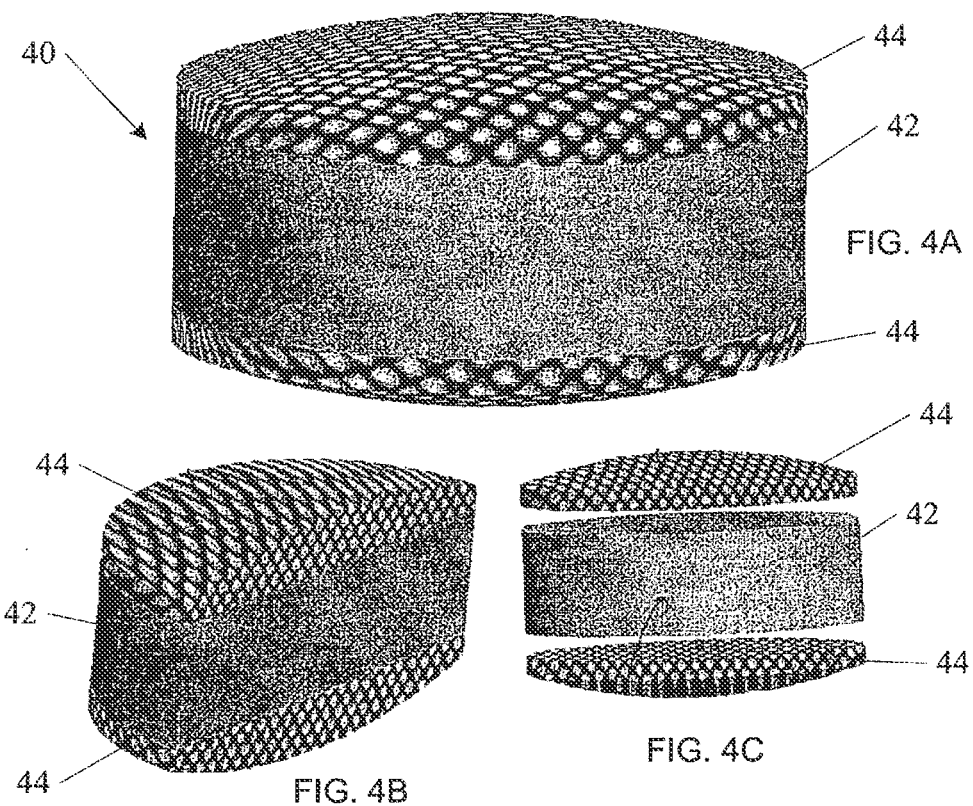

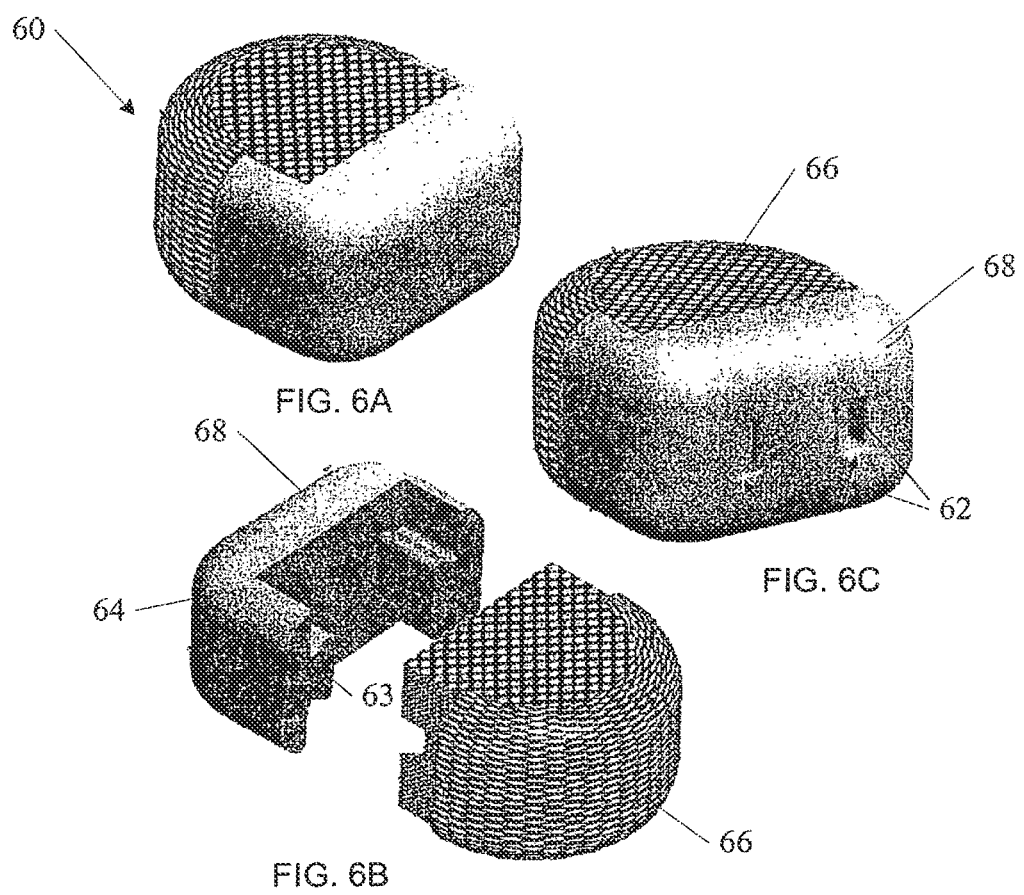

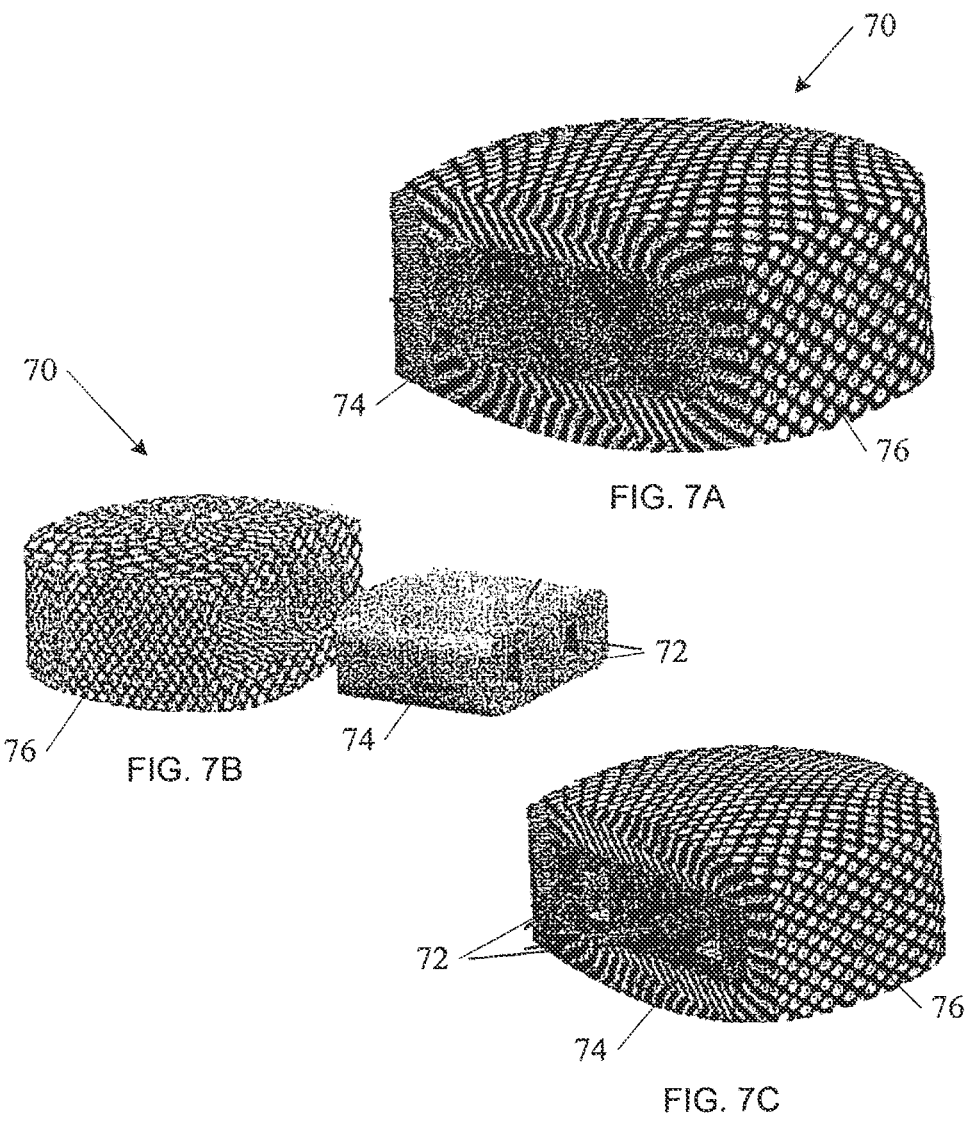

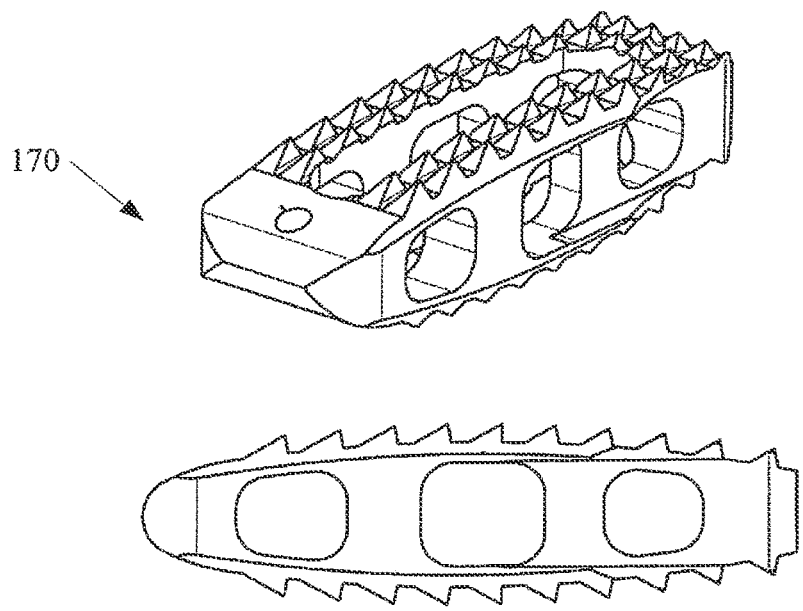
FIG. 17
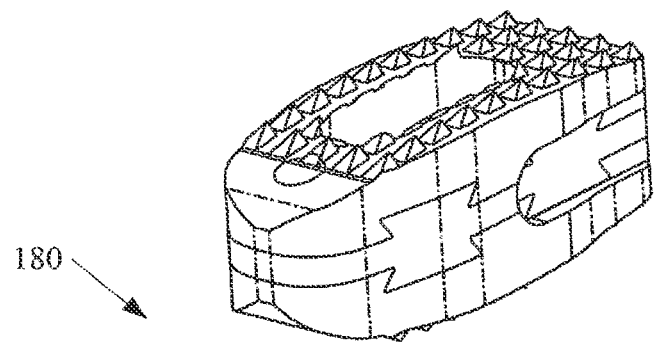
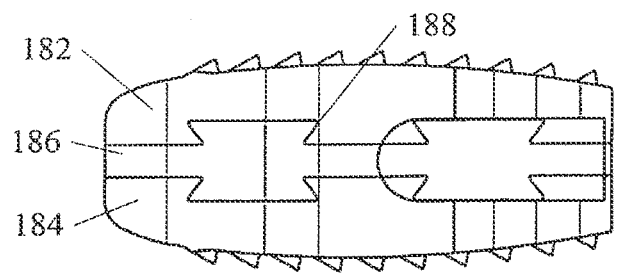
FIG. 18

POROUS BIOCOMPATIBLE POLYMER MATERIAL AND METHODS

CROSS REFERENCE TO RELATED APPLICATIONS

This application is a continuation of U.S. patent application Ser. No. 12/666,216 which has a filing date of Oct. 20, 2010, which is a 371 U.S. National Phase of International Patent Application No. PCT/US2009/000604, which has an international filing date of Jan. 30, 2009, which claims the benefit of U.S. Provisional Application No. 61/025,426, filed on Feb. 1, 2008, all of which are incorporated herein by reference in their entireties.

TECHNICAL FIELD

The present structures and methods relate to porous polymer materials and methods for making porous polymer materials and structures. Example structures include, but are not limited to, spacers for spinal fusion, Craniomaxillofacial (CMF) structures, other materials and structures for bone replacement.

BACKGROUND

Spinal fusion is a common technique used to treat chronic back pain caused by degenerated or herniated disk. The technique involves the removal of a disc between two vertebrae and replacing it with an intervertebral spacer. The intervertebral spacer maintains spacing between the two vertebrae and preferably results in fusion through the spacer. The intervertebral spacers may be constructed of autogenic bone tissue taken from a patient's own bone. Allogenic spacers are constructed of bone harvested from donors. Artificial spacers are currently the most common spacer type and may be constructed of metallic material such as titanium or stainless steel or polymers such as polyetheretherketone (PEEK).

PEEK has recently become popular due to its biocompatibility and naturally radiotranslucent characteristics, resulting in limited interference with x-ray and CT imaging. However, while PEEK is biocompatible, bone treats it as a foreign body during the remodeling process and isolates it with a fibrous tissue capsule. This fibrous tissue prevents direct bony apposition and adhesion to the implant. Other materials, such as titanium, allow for direct bony apposition and ongrowth, but they are typically not radiotranslucent and it becomes difficult to assess the fusion formation.

Other areas where PEEK is used as an orthopedic biomaterial experience similar fibrous encapsulation. Such indications include custom machined bodies that are used to fill defects in the skull and cranium. With PEEK, MRI and CT imaging is generally easier as compared to titanium, but the implant is never fully incorporated into the bone and soft tissue does not adhere to the implant.

Ceramic materials such as calcium phosphates, β-TCP, hydroxyapatites and the like allow for direct bony apposition much like titanium. However, they are typically limited in their strength and toughness. Therefore, it is desirable to construct a material that combines more of the desired properties from other individual materials described above, such as toughness and strength, less interference with MRI, X-ray or CT imaging, tissue adhesion, etc.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purposes of illustrating the polymeric porous bodies for promoting ingrowth/throughgrowth of the present application, there is shown in the drawings preferred embodiments. It should be understood, however, that the application is not limited to the precise arrangements and instrumentalities shown. In the drawings:

FIG. 1A illustrates a top view of a porous biocompatible material according to an embodiment of the invention.

FIG. 1B illustrates a top view of a porous biocompatible material according to the prior art.

FIGS. 4A, 4B, and 4C illustrate a front plan view, a front sectional perspective view, and a front exploded view, respectively, of a spacer having a solid core according to an embodiment of the invention.

FIGS. 6A, 6B, and 6C illustrate a top perspective view, a front perspective view, and a top perspective exploded view of another spacer with a solid portion according to an embodiment of the invention.

FIGS. 7A, 7B, and 7C illustrate a front perspective sectional view, a side perspective exploded view, and a front perspective view of another spacer according to an embodiment of the invention.

FIG. 17 illustrates a perspective view and a side view of another lumbar spinal spacer including a porous material according to an embodiment of the invention.

FIG. 18 illustrates a perspective view and a side view of another lumbar spinal spacer including a porous material according to an embodiment of the invention.

DETAILED DESCRIPTION OF THE INVENTION

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural and chemical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this patent application) nor the Abstract (set forth at the end of this patent application) is to be taken as limiting in any way as the scope of the disclosed invention(s).

Figure 2:
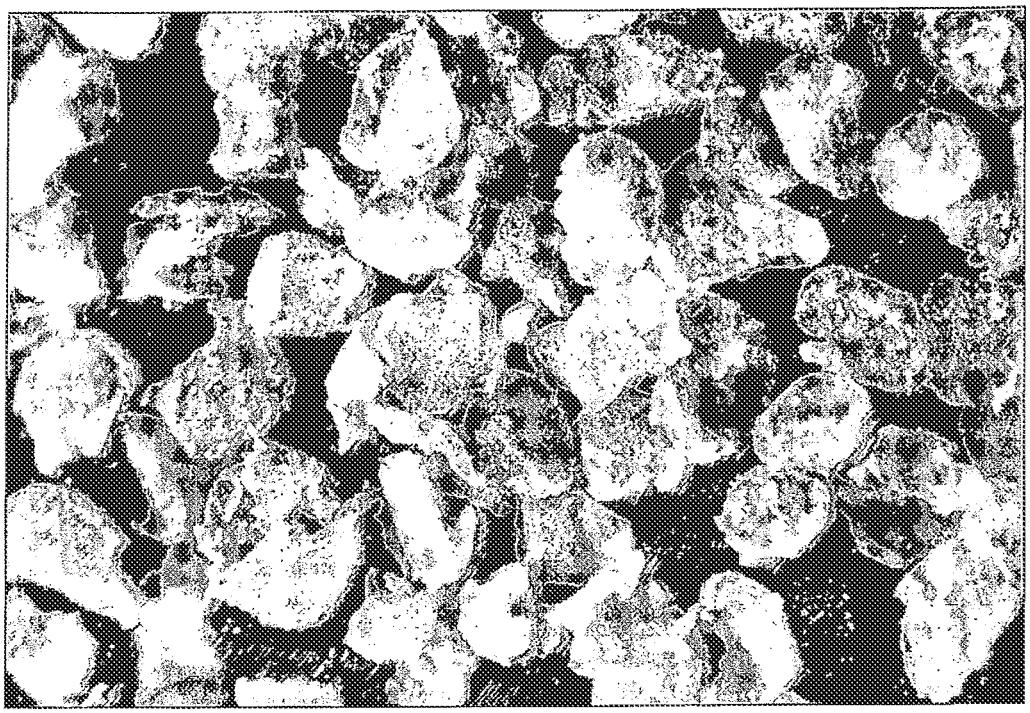
FIG. 2 illustrates a top plan view of PEEK granules with β-TCP on the surface according to an embodiment of the invention.

In reference to FIG. 1 and FIG. 2, there is illustrated the difference in final structure between a PEEK/β-TCP, tricalcium phosphate, mixture and a PEEK—only material placed in a 400° C. furnace for 5 minutes. Specifically, FIG. 1 shows PEEK granules that may be utilized to construct a porous spacer according to embodiments described in more detail below. The granules of the first preferred embodiment include a PEEK/beta-TCP mixture, having particles within a size range of 0.5-1.0 mm, with TCP applied at 400 degrees Centigrade for 5 minutes.

Inventive subject matter described herein relates to porous or partially porous body composites used to manufacture devices such as spacers for spinal fusion and tissue ingrowth surfaces in orthopedic devices, and to methods for making and using the porous bodies.

In one embodiment, a method is shown for making a porous intervertebral spacer usable in spinal fusion. The porous intervertebral spacers described herein include a main body made partially or totally of a composite. In selected embodiments, a main body includes polyetheretherketone, particles and a surface coating of beta tricalcium phosphate (β-TCP) covering at least a portion of the PEEK particles. Although PEEK is a polymer used in one example the invention is not so limited. Other embodiments utilize various thermoplastics other than or in addition to PEEK or combinations of polymers.

Porous spacer embodiments provide an initial stability and ultimately allow bony ingrowth from an inferior and superior vertebrae. In order to have good vascularization and bony ingrowth, pore structure of a porous spacer is generally interconnecting. In one example, a mean pore size as measured with mercury porosimetry, and is preferably in a range of 100-500 μm. The range of 100-500 μm is not intended to be limiting and at least a portion of the pores may fall outside of this range. It is generally understood that to allow mammalian tissue ingrowth, the pores must be large enough to allow a vascular network to be formed which at minimum requires passage of a red cell which is approximately 5-10 μm and thus this defines the desired lower size limit of at least a portion of the pores. A broader range of pores could thus be 5-5000 μm.

In one embodiment, a porous body formed using techniques described in the present disclosure are further perfused with patients' bone marrow and/or blood. The use of these autologous biologically active substances can provide a source of cells and growth factors that can accelerate the formation of bone and tissue into and on the porous structure and can also help to lead the precursor cells to differentiate down the desired path (i.e stem cells into osteoblasts that form bone). In one embodiment, the porous bodies are infused with allogenic biological substances to impart a similar effect. In selected embodiments, biologically active substances such as growth factors including, but not limited to BMP II, BMP VII and PDGF are infused. Synthetic small molecules that stimulate bone or tissue formation are included in some embodiments. Such small molecules include, but are not limited to, statins. Although individual additive substances are recited above, combinations of substances are also within the scope of the invention.

In some embodiments, the porous structure is modified to retain these biologically active substances and release them over an extended period of time or direct the location of their release and activity. In some embodiments the porous structure is coated with a substance that holds and then releases an active substance over a desired period. The materials used in such a coating include but are not limited to materials that hydrolytically degrade such as aliphatic polyesters such as PLA and PGA and hydrogels such as PEG and CMC. Alternately, in some embodiments the surface of the porous structures or treatments provides the desired release kinetics. Such surface structures include microporosity and changing the surface wettability.

In other embodiments a biologically active substance is applied to a separate carrier that is applied or inserted into the porous body of this invention. In one embodiment, a separate carrier is pre-inserted into a porous body. In one embodiment, a porous body is modified with areas of at least partially reduced porosity to reduce or prevent the release of the biologically active substance in certain directions. In one example, a thin outer shell of a non-porous polymer or other material is placed on a porous core to prevent the release of a biologically active substance in a radial direction. An advantage of such a configuration is realized in cervical fusion where the release of growth factors such as BMP II in a radial direction can lead to undesired tissue growth. In selected embodiments a non-porous material is made from a resorbable material so that the directionally controlled release is time dependant.

In one example method, polymer particles that have a specific particle size range are mixed with beta tricalcium phosphate (β-TCP), to form a mixture of polymer granules and coating powder. In one embodiment, the mixing provides an at least partial coating of the β-TCP around the surface of the polymer particles. Alternate materials that can be used to coat the polymer include, but are not limited to, calcium powders, bone powder, hydroyapatite, titanium (including titanium alloys and titanium oxides), barium salts and zirconium oxide. The mixture is placed in one or more molds at a temperature above a melting point of the polymer and held for a time effective to form bonding at the contact points of melted polymer particles.

In selected embodiments the powder coating the surface the of the polymer is subsequently removed and a microporous surface structure is obtained, the mircopores resulting from the volume previously occupied by the powder coating particles. An effective pore size of this microporous structure is in range of 0.1 and 100 microns.

In one example, the β-TCP powder inhibits, slows or in some embodiments, prevents the flow of polymer material above the melt temperature and causes the polymer particles to bead. An end product is a continuously porous material with a specific geometry that generally replicates the geometry of the mold. Examples of polymer material include, but are not limited to, PEEK, carbon reinforced PEEK, PEKK, PAEK family, PEK PEKK, PEKEKK, PCL, PLA, PGA, polyphenylene, self-reinforced polyphenylene, polyphenylsulphone, polysulphone, PET, polyethylene, polyurethane or other biocompatible polymers.

In some embodiments, additional materials are incorporated into the porous body. In one embodiment, the polymer particles are fused throughout a reinforcing structure. This reinforcing structure could be made from any known biocompatible material including titanium and stainless steel or the polymer itself and can provide additional mechanical strength to the porous body. In another embodiment, radiopaque materials are incorporated to provide selective areas of radiopacity so the location of the body can be visualized with X-rays or CT. These radiopaque materials include, but are not limited to, biocompatible metals (e.g. titanium aluminum nitride (TAN), titanium aluminum vanadium (TAV), tantalum, gold, barium, titanium, stainless steel), barium sulfate, zirconium oxide and radiopaque dyes. In other embodiments, the radiopaque material is used to mechanically reinforce the porous structure.

In some embodiments, the porous structure is selectively compressed in selective areas to impart increased mechanical strength. This compression is achieved through a combination of heat and or pressure. Methods to produce this heat and pressure include but are not limited to ultrasonics, radio frequency heating, induction heating, lasers or direct heating. These areas of reinforcement may form features for engagement with an instrument or structural ribs.

EXEMPLARY EMBODIMENTS

Porous PEEK Method

One process embodiment creates porous intervertebral spaces. The process embodiment includes using a polymer in particulate form. The particle size is in a range of 0.25-1.0 mm. This range is not intended to be limiting and other particle sizes can be used. The particles are mixed with β-TCP at a ratio of 90% polymer 10% β-TCP. The particle size of β-TCP is in a range of 0.01-0.1 mm. The particles are placed in a container and are mixed thoroughly. This mixing can be performed using a standard lab vortex shaker. The shaking allows the smaller β-TCP particles to at least partially cover the surface of the polymer particles. A sieve with a mesh size larger than β-TCP particle size but smaller than polymer particle size is used to remove the excess β-TCP particles. The resulting powder mix includes polymer particles coated with β-TCP. The purpose of the β-TCP is to prevent the polymer particles from flowing freely when heated above melting point. The presence of β-TCP causes the particles to bead and to prevent flow at or above melt point of the polymer. This allows for strong bonding between polymer particles while maintaining the interstitial space. When cooled, the final material defines an interconnecting porous polymer with β-TCP coating. The resulting material has the interconnecting porous structure for boney ingrowth and a β-TCP coating to produce a calcium rich surface for better osteoconduction.

As discussed above, in selected embodiment, the β-TCP or other coating powder is later removed from exposed surfaces within pores via an acid leaching, a selective solvent process, or another powder removal process. In this case the surface is calcium poor but has a microporous structure that can be advantageous from a wettability and cellular attachment perspective.

FIGS. 1A and 1B illustrate the difference in final structure between a PEEK/β-TCP mixture and a PEEK-only material placed in a 400° C. furnace for 5 minutes. FIG. 1A illustrates an interconnecting sample formed using methods described above with β-TCP on the surface. The particle size and the amount of the mixed particles inside the mold determine the porosity. The final mold geometry determines the final porous component size and shape.

FIG. 1B illustrates a collapsed structure of PEEK particles at the same temperature and time where no coating particles such as β-TCP were used. As can be seen from the Figures, interstitial spaces are more greatly preserved when coating particles such as β-TCP are included prior to melting the mixture. The process embodiments described herein allow for stronger bonding compared to standard sintering methods at quicker processing time. Because sintering involves heating the material below melt point, the bonding between the particles is not as strong as materials bonded by heating the particles to above melting point.

FIG. 2 illustrates PEEK polymer particles coated with β-TCP powder by mixing 90% PEEK and 10% β-TCP by weight prior to melting. The mixture was placed in a 250 μm sieve to remove the excess β-TCP powder. The resulting powder consisted of PEEK granules covered with β-TCP powder, as shown in FIG. 2.

Although a PEEK polymer coated with β-TCP powder is described in the exemplary embodiment above, the invention is not so limited. Other polymers coated with other power particles are within the scope of the invention. One of ordinary skill in the art, having the benefit of the present disclosure will recognize that with other polymers and other coating powders, other processing conditions such as heating temperature and time, etc. can be adjusted to form porous polymer structures using alternative materials.

Monolithic Porous Structure

Figure 3:
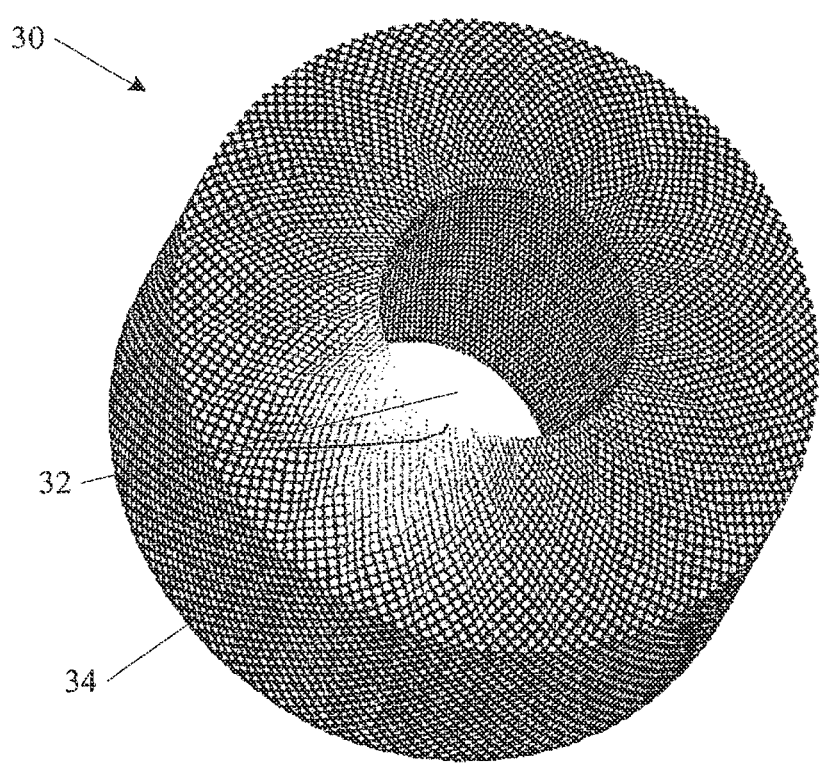
FIG. 3 illustrates a top perspective view of a porous spacer with a through hole according to an embodiment of the invention.

One embodiment of the Porous PEEK structure is a prosthesis for interverbral body fusion that is made completely of porous PEEK, as is shown in FIGS. 3, 11, and 12A-12B. The prostheses can assume the form of a variety of external shapes in order to optimize endplate coverage. The superior and inferior surfaces may include pyramidal or unidirectional teeth or ridges molded in order to increase the devices' primary stability in the intervertebral space. Some embodiments, one of which is as spacer 30 in FIG. 3, defines one or more axial holes 32 to allow solid bony through growth. In one embodiment, lateral windows in a side 34 of the spacer 30 are further provided to enhance the assessment of fusion via radiograph or other suitable techniques. Although a generally cylindrical shape is shown in FIG. 3 as a monolithic porous structure example, other monolithic porous geometries such as solid cylinders, scaffold shapes, complex molded custom fitted shapes, etc. are within the scope of the invention.

Solid Core

FIGS. 4A, 4B and 4C illustrate an implant 40 for intervertebral body fusion. The implant 40 is constructed of a solid PEEK core 42 thermally bonded to porous endplates 44. This implant embodiment 40 serves to increase the ultimate axial compressive strength of the implant while maintaining the benefits of bony ingrowth and primary stability.

Figure 5A:
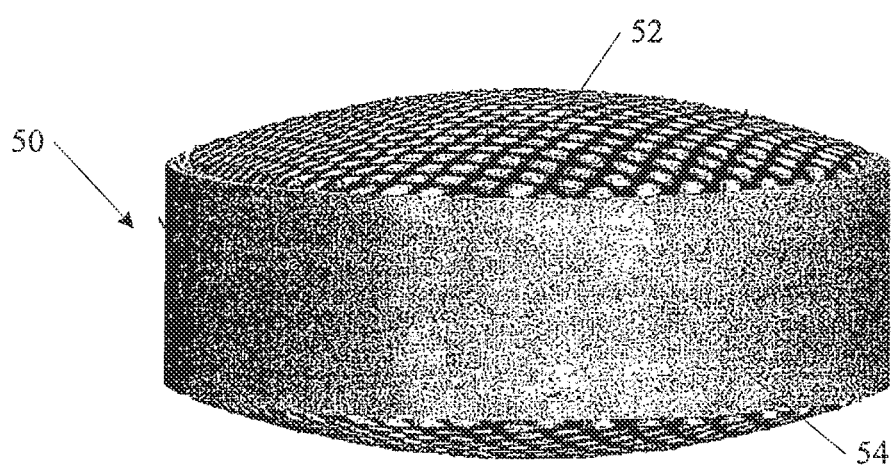
FIGS. 5A, 5B, and 5C illustrate a front plan view, a front perspective sectional view, and a front perspective exploded view of a spacer having a solid band according to an embodiment of the invention.
Figure 5B:
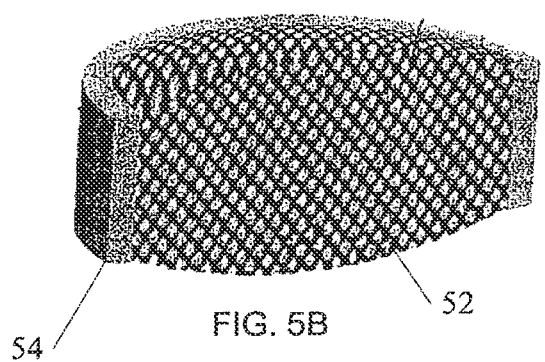
Figure 5C:
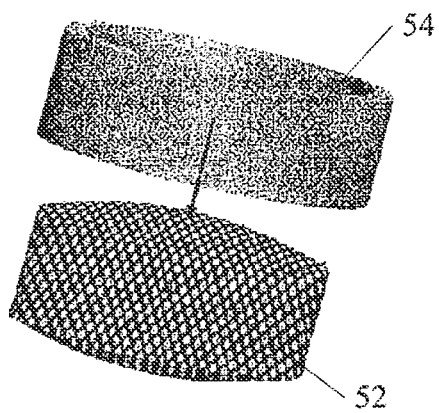

FIGS. 5A, 5B and 5C illustrate an implant embodiment 50 that includes a porous PEEK main body 52 and a solid band 54, annularly positioned about the main body 52.

Solid Implant Holder

During conventional implantation of an intervertebral body device, it is desirable that a surgeon maintains precise control of the implant. One important part of such control is achieved by tightly gripping an implant. It is desirable for the steps of gripping and releasing to be such that an introduction profile of the spacer is not increased or otherwise changed in any significant way.

In FIGS. 6A, 6B and 6C, an implant holding feature 62 is integrated into a solid portion 64 of the implant embodiment 60 that is mechanically connected to a porous component 66. An example of a mechanical connection includes tabs 63 that fit into corresponding slots. Although tabs 63 are shown, other configurations of mechanical connections such as other interference fit geometries, bayonette fasteners, etc. The embodiment of FIGS. 6A, 6B and 6C shows the solid portion 64 extending from an inferior to the superior surface of one side 68 of the implant which can be positioned to bear the greatest axial loads and to increase a shear strength of the implant by reinforcing the porous component 66.

In the embodiment show, the holding feature 62 includes a pair of slots. In one embodiment a pair of slots such as slots 62 are configured to interface with a surgeon's tool to provide precise control. One of ordinary skill in the art will recognize that a number of other possible holding feature configurations such as single slots, protruding features, etc. are within the scope of the invention.

FIGS. 7A, 7B and 7C, illustrate another example of a holding feature 72. In the example of FIGS. 7A-C, the holding feature 72 is integrated into a solid core 74 of the implant 70. Similar to embodiments described above, the implant 70 is composed of a solid portion 74 which includes the holding feature 72, and a porous polymer portion 76 formed using methods described in embodiments above.

Figure 10:
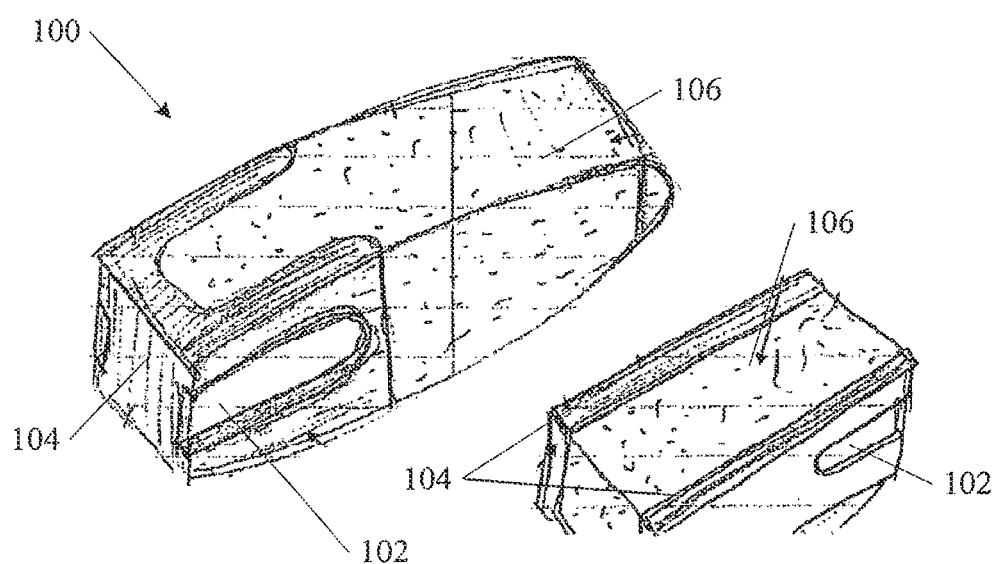
FIG. 10 illustrates a side perspective view and a side perspective sectional view of a spacer including an instrument engagement feature according to an embodiment of the invention.

FIG. 10 illustrates another example embodiment 100 including an implant holder feature 102 that is integrated into an exterior geometry of a solid portion 104 which is bonded to a porous body 106. As can be seen from the examples, a number of possible configurations for implants and holding features are contemplated.

Porous Endplate Feature on a Device for Disc Arthroplasty

Figure 8:
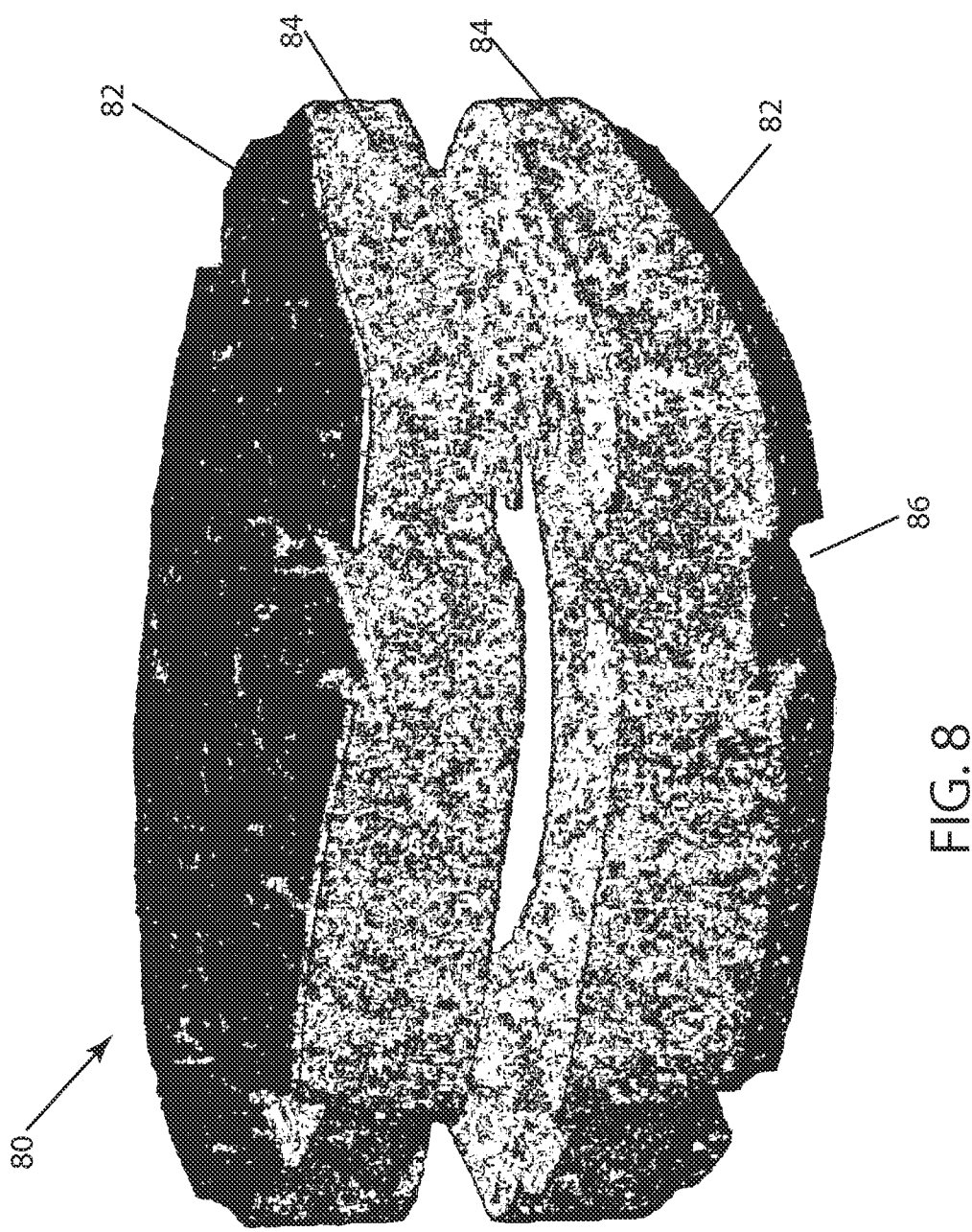
FIG. 8 illustrates a front perspective view of a total disc replacement implant for disc arthroplasty according to an embodiment of the invention.

FIG. 8 illustrates one embodiment of an intervertebral prosthesis for disc arthroplasty at 80 that includes porous PEEK endplates 82 thermally bonded to solid PEEK 84 with lateral insertion slots 86.

Multi-Component Constructs

Figure 9A:
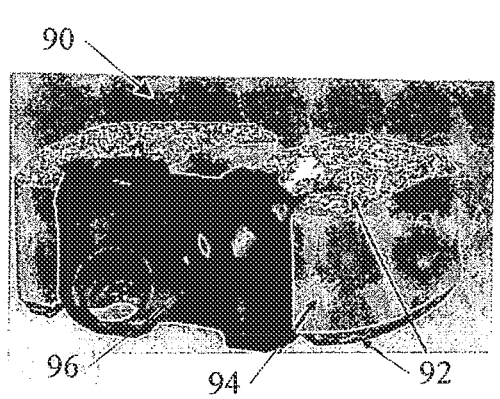
FIGS. 9A, 9B, and 9C illustrate a front perspective view, a top plan view, and a side perspective view of a spacer and a fixation plate according to an embodiment of the invention.
Figure 9B:
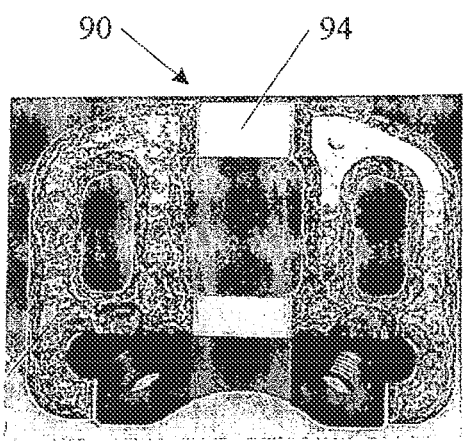
Figure 9C:
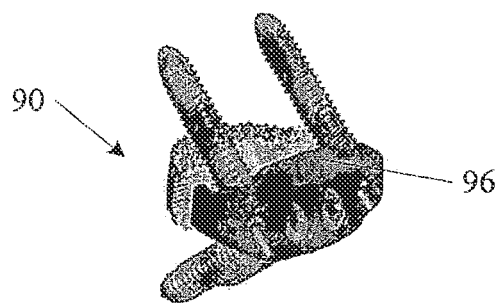

FIGS. 9A, 9B and 9C illustrates one embodiment of an intervertebral spacer 90 with integrated fixation showing porous PEEK endplates 92 thermally bonded to a solid PEEK core 94 and mechanically connected to a metallic plate 96. A central distractor slot aides insertion.

Spinal Spacer Example Configurations

FIGS. 11-20 illustrate a number of example configurations of lumbar spinal spacers including at least a portion of porous polymer material formed using methods described in the present disclosure. Although a number of examples are shown, the invention is not so limited. In each example, the entire spacer may be formed from porous polymer material as described, or only a portion of the spacer may be formed from porous polymer material as described. As described herein, other material configurations include a solid portion bonded, mechanically joined, or otherwise attached to a porous portion. Example solid portions include solid cores, solid bands, solid skins, etc. attached to a porous polymer portion.

Figure 21:
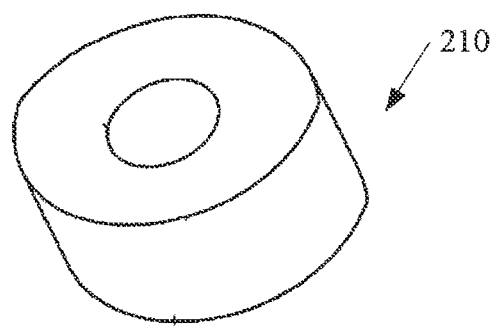
FIG. 21 illustrates a perspective view of a cervical spinal spacer including a porous material according to an embodiment of the invention.
Figure 22:
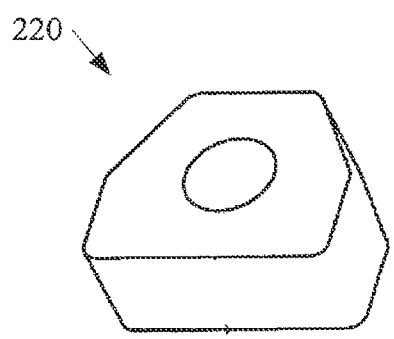
FIG. 22 illustrates a perspective view of another cervical spinal spacer including a porous material according to an embodiment of the invention.
Figure 23:
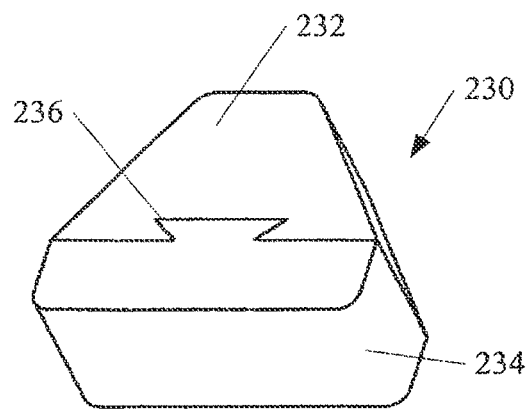
FIG. 23 illustrates a perspective view of another cervical spinal spacer including a porous material according to an embodiment of the invention.

FIGS. 21-23 illustrate a number of example configurations of cervical spinal spacers including at least a portion of porous polymer material formed using methods described in the present disclosure. Similar to discussion of lumbar spacers, a number of configurations utilizing porous polymer materials are within the scope of the invention. Configurations that utilize portions of solid material as described above are also included.

Figure 11:
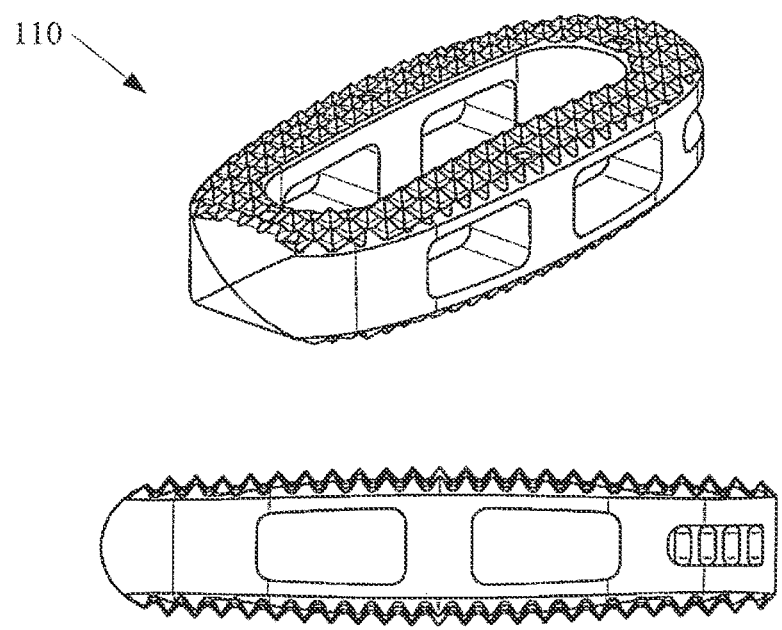
FIG. 11 illustrates a perspective view and a side view of a lumbar spinal spacer including a porous material according to an embodiment of the invention.
Figure 12:
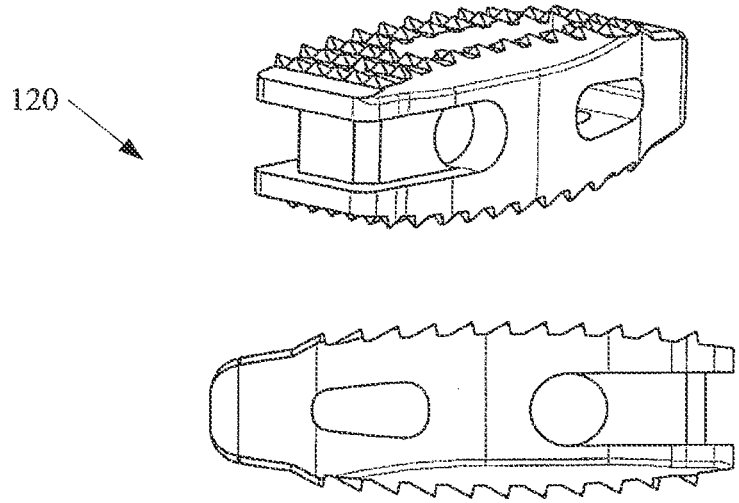
FIG. 12 illustrates a perspective view and a side view of another lumbar spinal spacer including a porous material according to an embodiment of the invention.
Figure 13:
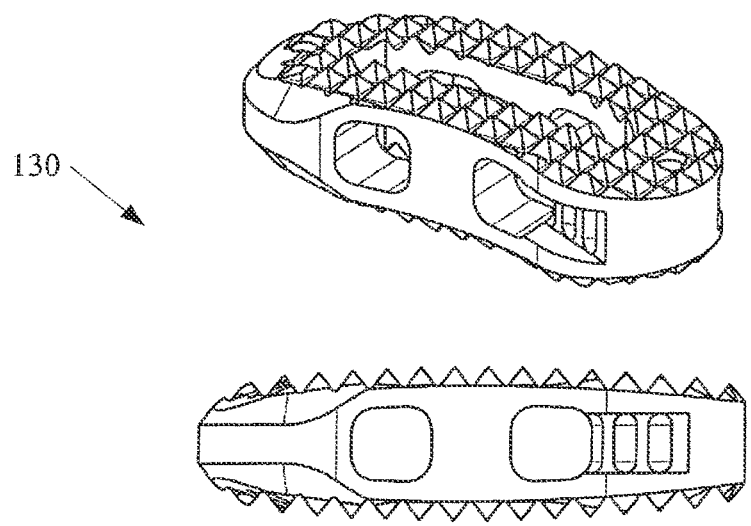
FIG. 13 illustrates a perspective view and a side view of another lumbar spinal spacer including a porous material according to an embodiment of the invention.
Figure 14:
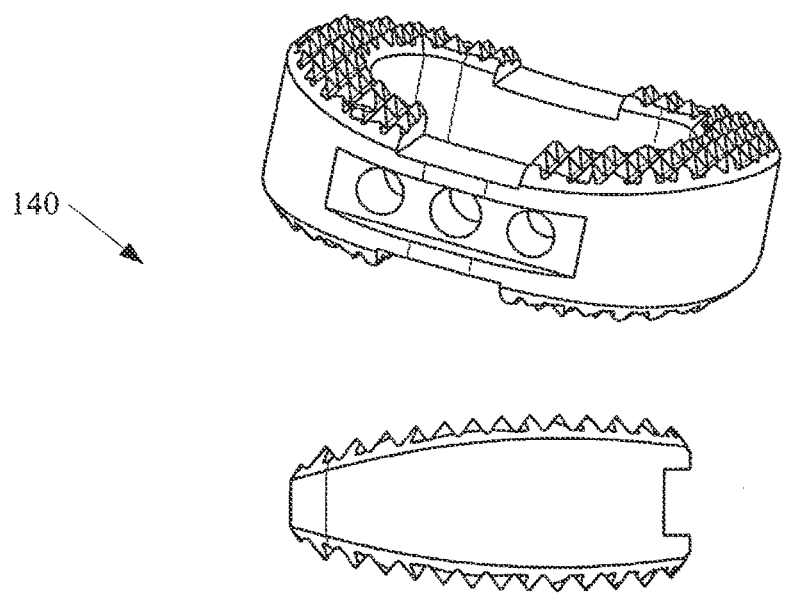
FIG. 14 illustrates a perspective view and a side view of another lumbar spinal spacer including a porous material according to an embodiment of the invention.
Figure 15:
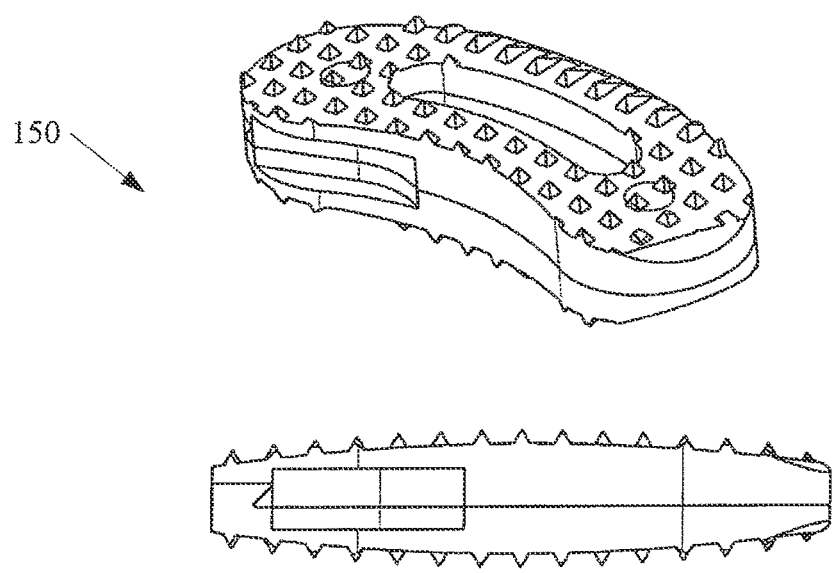
FIG. 15 illustrates a perspective view and a side view of another lumbar spinal spacer including a porous material according to an embodiment of the invention.
Figure 16:
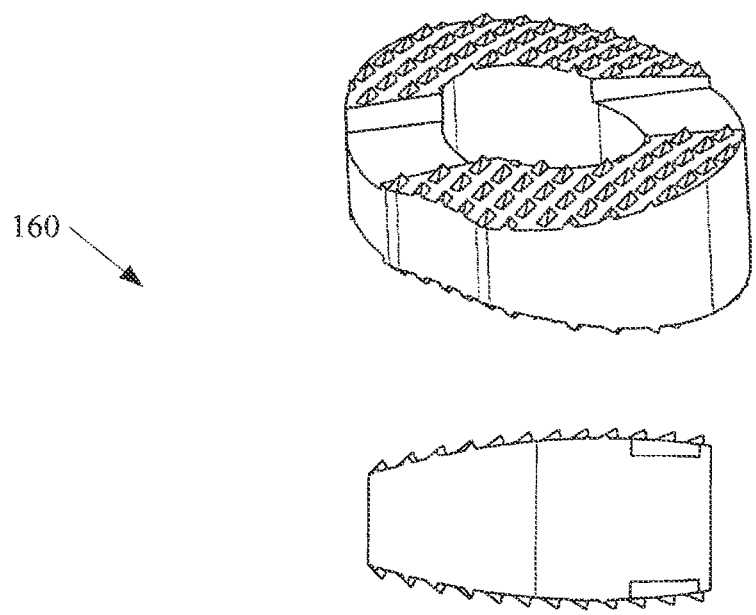
FIG. 16 illustrates a perspective view and a side view of another lumbar spinal spacer including a porous material according to an embodiment of the invention.

FIG. 11 shows a spacer 110 that includes at least a portion of porous polymer material. FIG. 12 shows a spacer 120 that includes at least a portion of porous polymer material. FIG. 13 shows a spacer 130 that includes at least a portion of porous polymer material. FIG. 14 shows a spacer 140 that includes at least a portion of porous polymer material. FIG. 15 shows a spacer 150 that includes at least a portion of porous polymer material. FIG. 16 shows a spacer 160 that includes at least a portion of porous polymer material. FIG. 17 shows a spacer 170 that includes at least a portion of porous polymer material.

FIG. 18 shows a multi-component spacer 180 that includes at least a portion of porous polymer material. A first portion 182, a second portion 184, and a third portion 186 are shown attached together. In the embodiment shown, the portions are attached using a mechanical attachment 188. In one example, the mechanical attachment includes a dovetail configuration as shown in the figure. Although a dovetail is an easy and effective mechanical attachment, the invention is not so limited. Other geometries of mechanical attachments 188 are within the scope of the invention.

Figure 19:
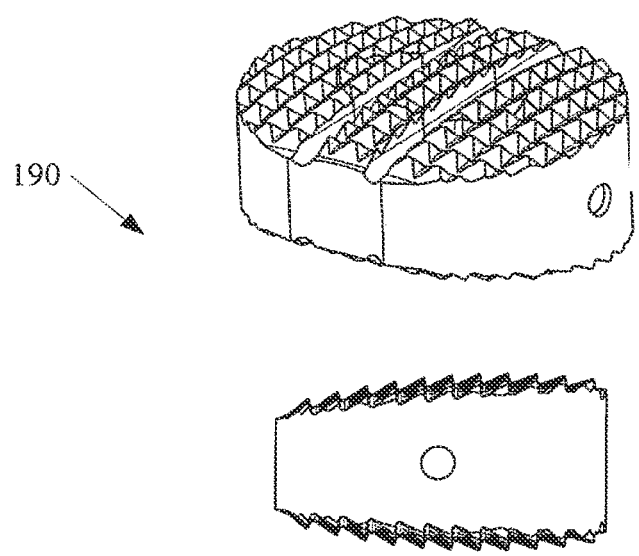
FIG. 19 illustrates a perspective view and a side view of another lumbar spinal spacer including a porous material according to an embodiment of the invention.
Figure 20:
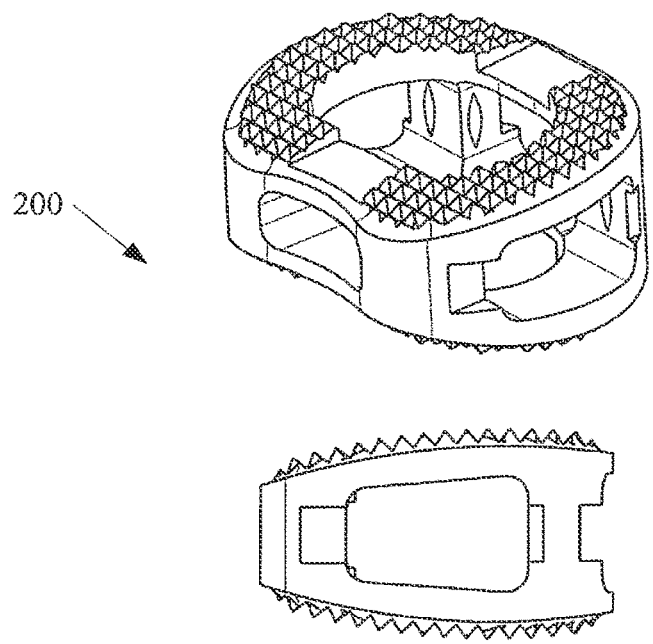
FIG. 20 illustrates a perspective view and a side view of another lumbar spinal spacer including a porous material according to an embodiment of the invention.

FIG. 19 shows a spacer 190 that includes at least a portion of porous polymer material. FIG. 20 shows a spacer 200 that includes at least a portion of porous polymer material. FIG. 21 shows a spacer 210 that includes at least a portion of porous polymer material. FIG. 22 shows a spacer 220 that includes at least a portion of porous polymer material.

FIG. 23 shows a multi-component spacer 230 that includes at least a portion of porous polymer material. A first portion 234, and a second portion 236 are shown attached together using a mechanical attachment 236. Similar to spacer 180 described above, in one example the mechanical attachment 236 includes a dovetail arrangement or similar mechanical attachment.

Additional Surface Preparation

Embodiments described in the present disclosure can also include various finishing processes depending on desired final properties. One additional surface treatment includes using a plasma treatment with ionized oxygen or other gas. In selected embodiments, such a plasma treatment alters surface chemistry in a to increase wetability. Another surface treatment includes a Hydroxylapatite (HA) coating to increase an osteoconductive potential of the implant surface. Another surface treatment includes a Calcium Phosphate Coating to increase the osteoconductive potential of the implant surface. Another surface treatment includes a titanium nitride coating to provide a surface desirable for bony ongrowth. Other surface treatments to provide a surface desirable for bony ongrowth include titanium or other biocompatible metal or oxide coatings applied by any of a number of processes such as physical vapor deposition, chemical vapor deposition, etc.

Alternate Design Embodiments

Additional embodiments include an incorporation of larger, discrete β-TCP, titanium or other osteoconductive particles to the coating powder mix. These larger osteoconductive particles are of approximately the same size as the thermoplastic material. In selected embodiments, the discrete osteoconductive particles enhance the osteoconduction properties of the porous material already coated with β-TCP powder. One source of osteoconductive particles include CronOS™ manufactured by Synthes.

Alternate Applications

As noted above, other uses for the porous material include scaffolds for tissue ingrowth applications other than spinal spacers. The porous material as described in embodiments above is further usable as a bone void filler in a number of applications where bone ingrowth is desired in anatomical locations under physiological mechanical stresses. An example of an application other than a spinal spacer includes manufacturing at least part of an implant suitable for use in cranial or craniofacial defect repair.

For applications other than those described in spinal spacer examples above, it may be desirable to modify mechanical properties of the porous polymer such as modulus, shear strength, etc. Changing the polymer and/or coating powder results in different mechanical properties as desired. In selected embodiments, porous polymer structure properties are modified such that they are suitable for soft tissue ingrowth.

Alternate Materials/Coatings

The main bodies, or portions thereof, of some of the spacer embodiments of the present invention are formed from PEEK polymer or other polymers. In addition to various polymer choices, coating powder materials can be selected that are other than β-TCP. Alternative powders such as Barium Sulfate (BaSO4) or Strontium Carbonate (SrCO3) have similar effects on the polymers during heating above the melt point as β-TCP.

Mechanical Testing

Figure 24:
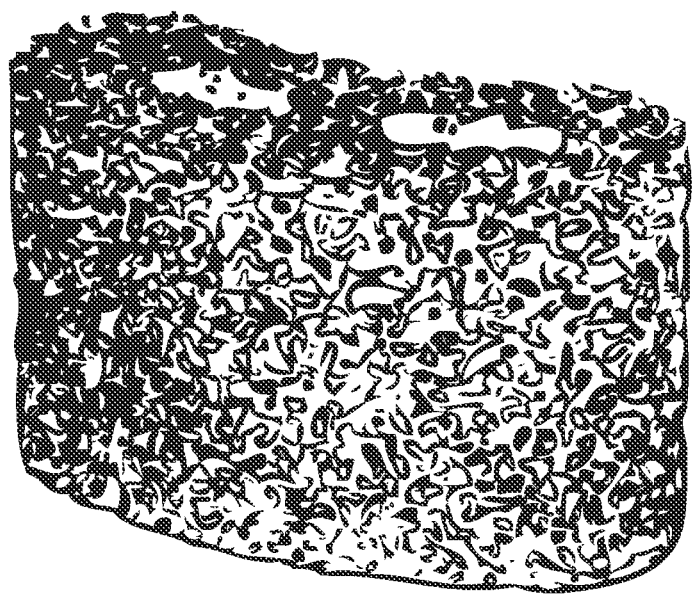
FIG. 24 illustrates a front perspective view of a porous lumbar spacer according to an embodiment of the invention.
Figure 25A:
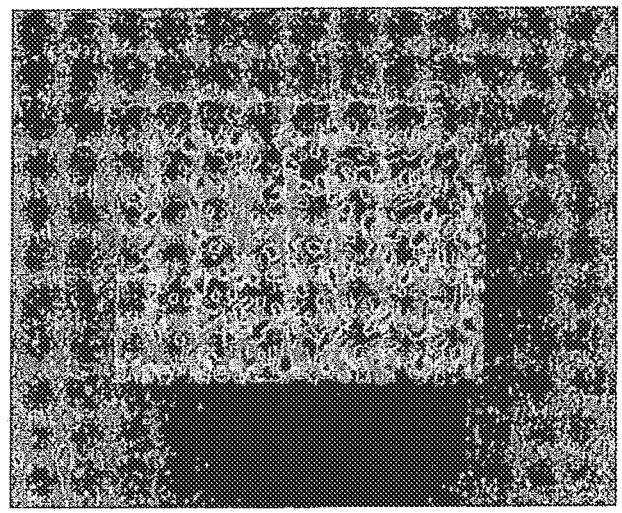
FIGS. 25A and 25B illustrate a side plan view and a top plan view, respectively, of a porous spacer according to an embodiment of the invention.
Figure 25B:
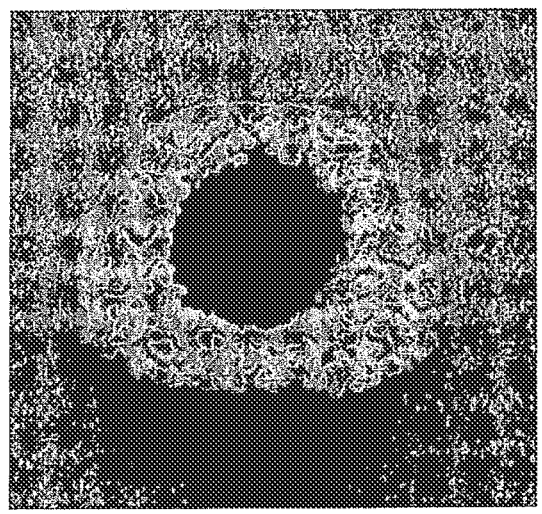
Figure 26:
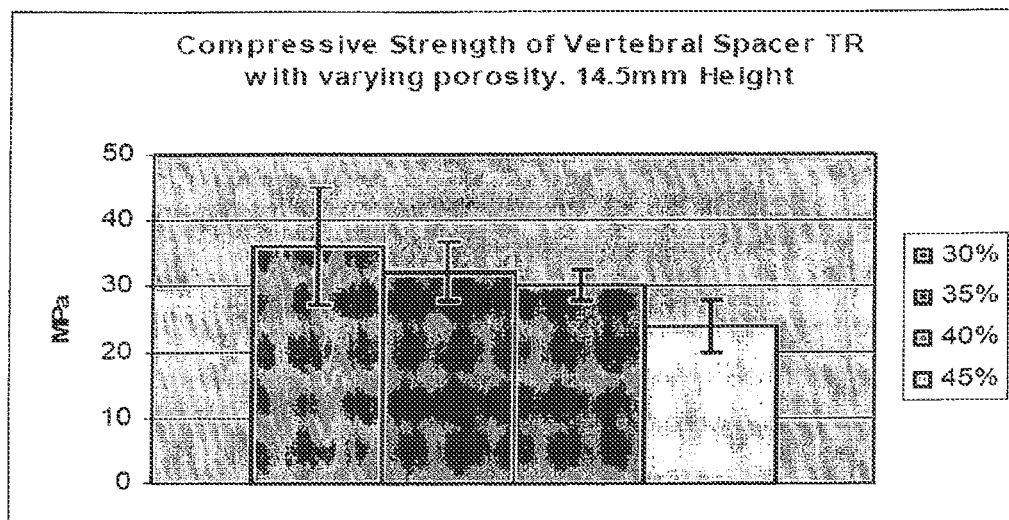
FIG. 26 illustrates a graph showing the relationship between the compressive strength and the porosity of the spacer of FIG. 24.
Figure 27:
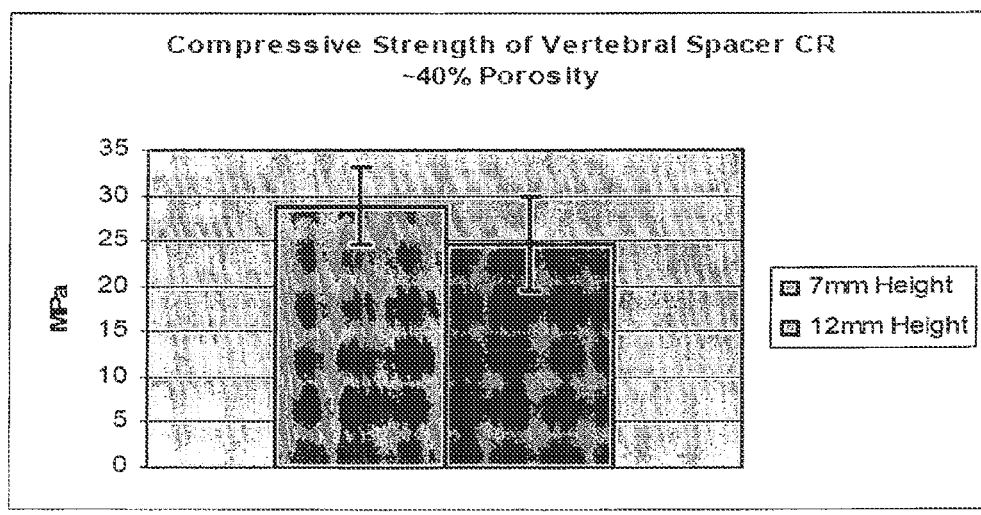
FIG. 27 illustrates a graph showing the relationship between the compressive strength of the spacer of FIG. 25A-25B.

In reference to FIGS. 24 and 25A-25B, porous PEEK spacers were created by placing the PEEK/β-TCP powder described above into a mold. The amount of powder mixture placed inside the mold determined the porosity of the final structure. The particle size range determined the pore size. Two types of samples with varying surface areas and heights were made to form spacers similar in geometry to those known in the industry. The final samples were tested for compressive strength. FIG. 26 illustrates a graph showing the relationship between the compressive strength and the porosity of the spacer of FIG. 24, while FIG. 27 illustrates a graph showing the relationship between the compressive strength of the spacer of FIG. 25A-25B, having a 40 percent porosity, and the height of the spacer.

Figure 28A:
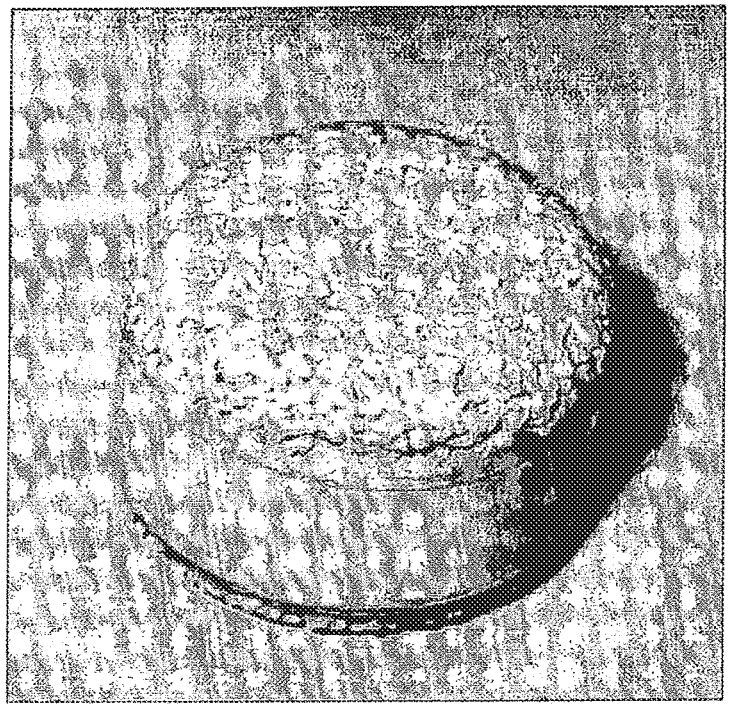
FIGS. 28A and 28B illustrate a front perspective views of sample structures with solid cores according to an embodiment of the invention.
Figure 28B:
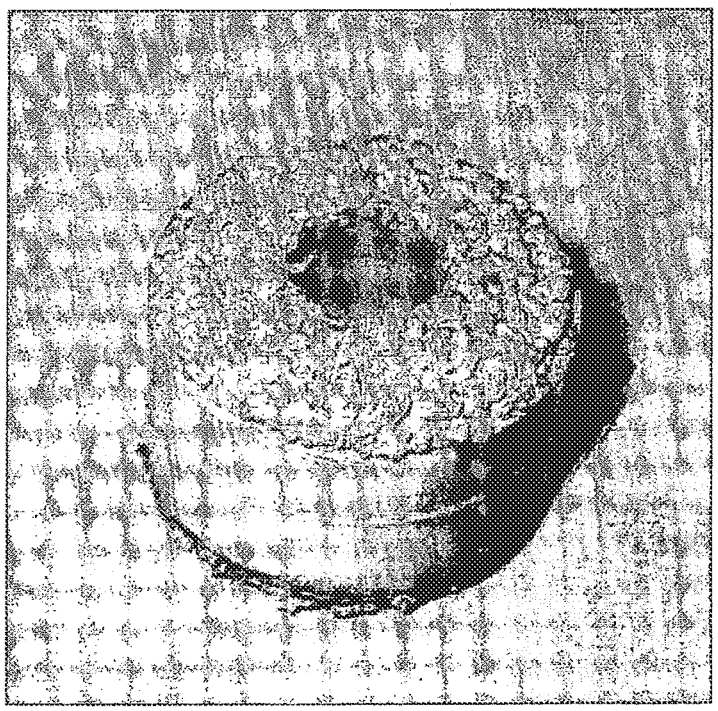
Figure 29:
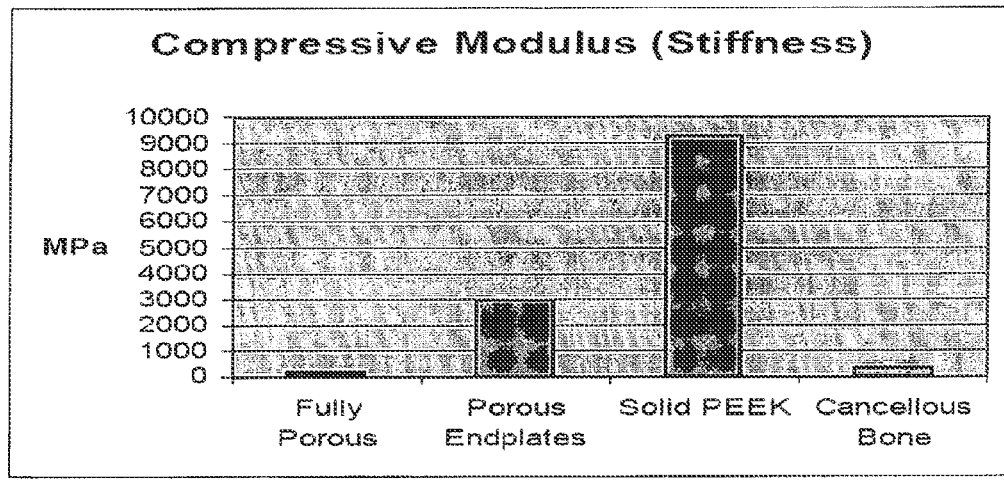
FIG. 29 illustrates a graph showing the differences between the compressive moduli (stiffnesses) of various structures according to an embodiment of the invention.
Figure 30:
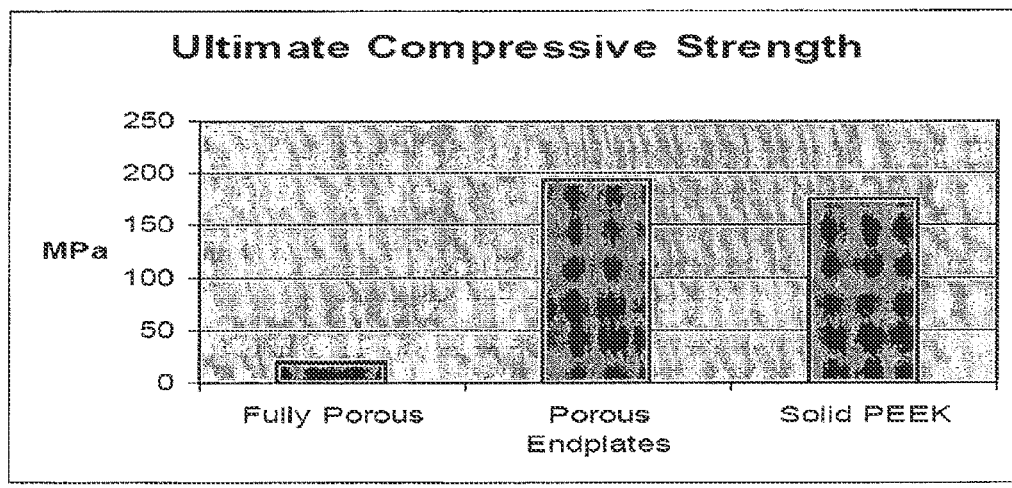
FIG. 30 illustrates a graph showing the ultimate compressive strengths of various structures according to an embodiment of the invention.

In reference to FIGS. 28A-28B, composite samples, as opposed to the fully porous samples, were made in which a solid PEEK cylinder was sandwiched between two porous PEEK endcaps. The solid core gives the composite it's higher compressive strength and the porous endcaps allow bone ingrowth from top and bottom vertebrae. FIG. 29 is a graph showing the differences between the compressive moduli (stiffnesses) of a spacer formed entirely from porous PEEK, a spacer formed from solid PEEK spacer and having porous PEEK endplates (such as the spacer illustrated in FIGS. 28A-28B), a spacer formed entirely from solid PEEK, and a spacer formed entirely from cancellous bone. FIG. 30 illustrates a graph showing the ultimate compressive strengths of a spacer formed entirely from porous PEEK, a spacer formed from solid PEEK and having porous PEEK endplates (such as the spacer illustrated in FIGS. 28A-28B), and a spacer formed entirely from solid PEEK.

While a number of embodiments of the invention are described, the above examples are not intended to be exhaustive. The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A method of forming a porous polymer material, comprising:
   forming a mixture of polymer granules and ceramic coating powder,
   wherein the polymer granules comprise polyaryletherketone (PAEK) polymers;
   wherein the ceramic coating powder comprises ceramic particles that coat the polymer granules;
   wherein the ceramic particles are smaller than the polymer granules;
   wherein the ceramic particles do not melt at a melting temperature of the polymer granules;
   heating the mixture to a temperature above the melting temperature of the polymer granules;
   controlling flow of molten polymer as a result of the ceramic coating powder substantially preserving interstitial spaces in the mixture; and
   cooling the mixture to form a porous body having bonds at contact points of the coated polymer granules.

2. The method of claim 1, further comprising using the porous body to form a spacer for spinal fusion.

3. The method of claim 1, wherein a the ceramic coating powder includes ceramic particles selected from the group consisting of barium sulfate ($BaSO_4$) and strontium carbonate ($SrCO_3$).

4. The method of claim 1, further comprising using the porous body to form a craniomaxillofacial (CMF) structure.

5. The method of claim 1 further comprising:
   plasma treating a surface of the porous polymer material using ionized oxygen.

6. The method of claim 1, further comprising coating a surface of the porous polymer material with hydroxyapatite.

7. The method of claim 1, further comprising coating a surface of the porous polymer material with calcium phosphate.

8. The method of claim 1, further comprising coating a surface of the porous polymer material with titanium nitride.

9. The method of claim 1, further comprising selectively compressing the porous body.

10. The method of claim 1, further comprising incorporating a reinforcing structure into the porous body.

11. The method of claim 1, wherein forming the mixture of polymer granules and ceramic coating powder includes selecting a polymer material to match a mechanical property of the porous body to a corresponding mechanical property of adjacent tissue.

12. The method of claim 11, wherein the mechanical property includes an elastic modulus.

13. The method of claim 1, further comprising applying a biologically active substance to the porous body.

14. The method of claim 13, further comprising coating the porous body with a material configured to control the release of the biologically active substance.

15. The method of claim 1, wherein the polymer granules includes polyetheretherketone (PEEK) granules.

16. The method of claim 15, wherein the ceramic coating powder includes beta tricalcium phosphate ($\beta$-TCP).

17. The method of claim 16, wherein the mixture of polymer granules and-ceramic coating powder-is about 90% by weight polyetheretherketone (PEEK) and about 10% by weight beta-tricalcium phosphate.

18. The method of claim 1, further including substantially removing the ceramic coating powder through formed pores after the mixture has cooled.

19. The method of claim 18, wherein the formed pores have a mean pore size of 5 μm to 5000 μm.

20. The method of claim 18, wherein the formed pores have a mean pore size of 100 μm to 500 μm.

21. The method of claim 18, further comprising perfusing the formed pores with a biologically active substance.

\* \* \* \* \*